United States Patent [19]
Brown et al.

[11] Patent Number: 6,032,119
[45] Date of Patent: Feb. 29, 2000

[54] PERSONALIZED DISPLAY OF HEALTH INFORMATION

[75] Inventors: Stephen J. Brown, Mountain View, Calif.; Erik K. Jensen, Stockton, N.J.

[73] Assignee: Health Hero Network, Inc., Mountain View, Calif.

[21] Appl. No.: 08/784,740

[22] Filed: Jan. 16, 1997

[51] Int. Cl.[7] .................................................. G06F 15/42
[52] U.S. Cl. ................... 705/2; 705/9; 395/500; 600/300; 600/301; 600/483; 177/25.19
[58] Field of Search .................. 600/300; 177/25.19; 705/2, 9; 395/500

[56] References Cited

U.S. PATENT DOCUMENTS

| | | | |
|---|---|---|---|
| 4,347,568 | 8/1982 | Giguere et al. | 600/300 |
| 4,803,625 | 2/1989 | Fu et al. | 600/483 |
| 4,899,839 | 2/1990 | Dessertine et al. | 177/25.19 |
| 5,065,315 | 11/1991 | Garcia | 705/2 |
| 5,410,471 | 4/1995 | Alyfuku et al. | 600/300 |
| 5,542,420 | 8/1996 | Goldman et al. | 600/301 |
| 5,583,758 | 12/1996 | McIlroy et al. | 705/2 |
| 5,594,637 | 1/1997 | Eisenberg et al. | 705/2 |
| 5,680,590 | 10/1997 | Parti | 395/500 |

*Primary Examiner*—Allen R. MacDonald
*Assistant Examiner*—Jagdish Patel
*Attorney, Agent, or Firm*—Lumen Intellectual Property Services

[57] ABSTRACT

Delivery of health information to a patient suffering from a chronic condition is personalized by displaying the health information directly on a customized image of a body. The patient's medical record, standards of care for the condition, prescribed treatments, and patient input are applied to a generalized health model of a disease to generate a personalized health model of the patient. The personalized health model comprises an HTML file encoding an image map of a body. The body image illustrates the health condition of the individual patient. Preferably, data is collected from health provider sources and stored in a database on a server at a service provider site. The data is processed at the server, and is displayed in the patient's home using a TV connected to a multimedia processor. The multimedia processor connects the television set to a communications network such as the Internet. Applications include preventive care of chronic diseases such as diabetes and asthma.

42 Claims, 8 Drawing Sheets

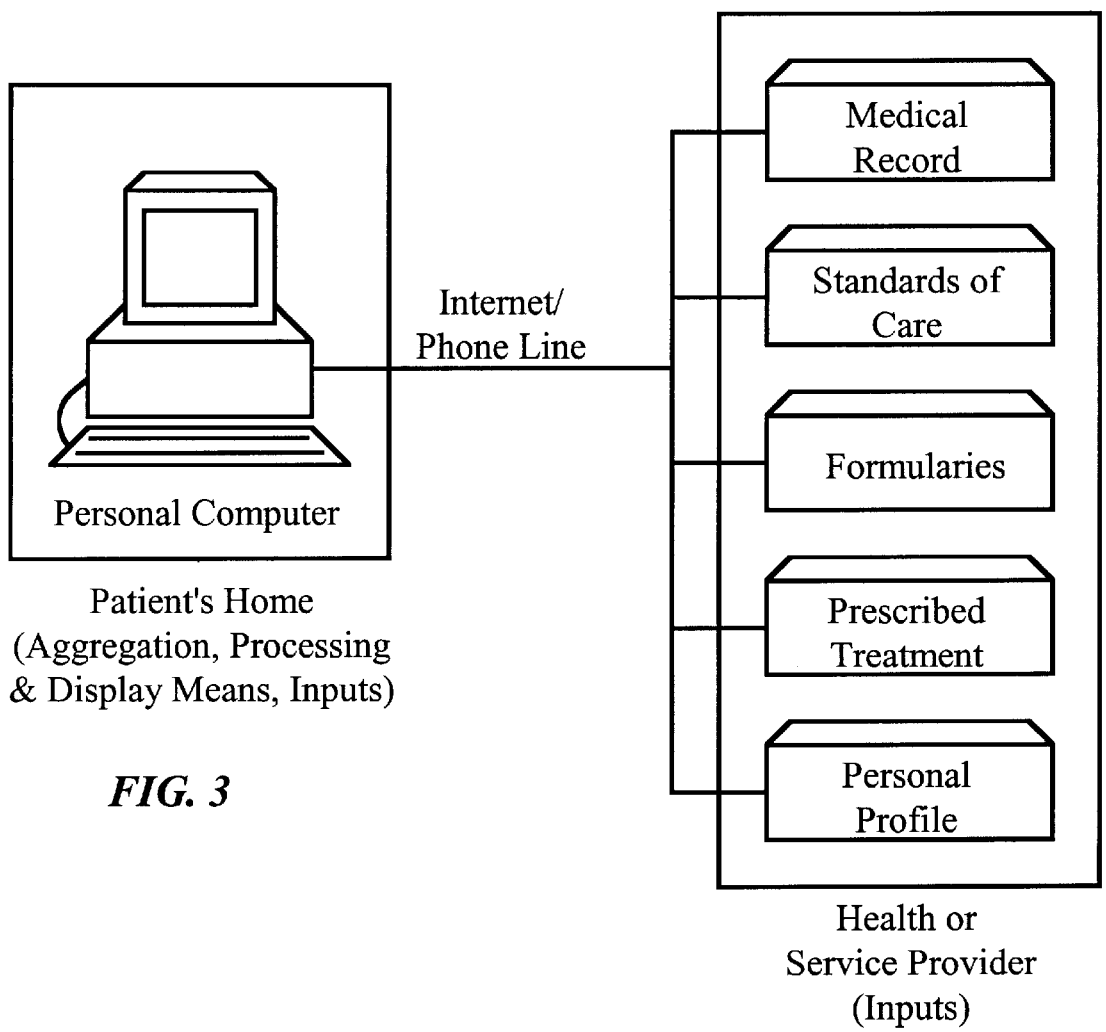
FIG. 3
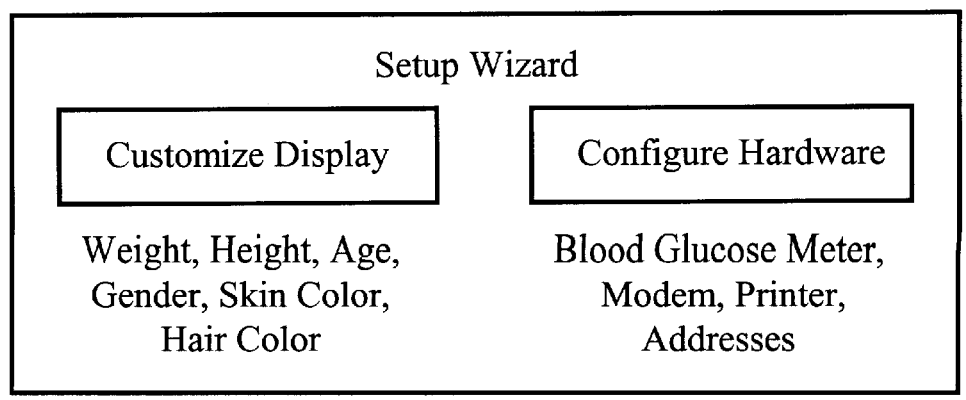
FIG. 4-A

*FIG. 4-B*
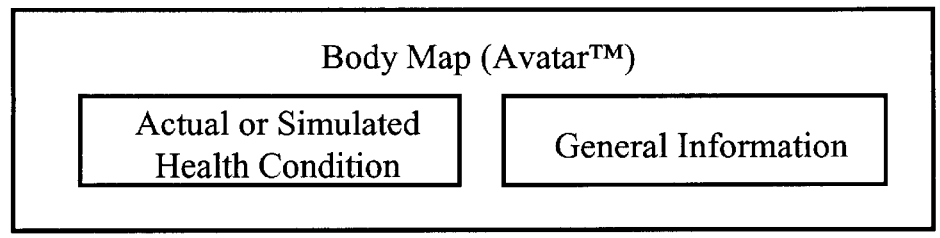
*FIG. 4-C*
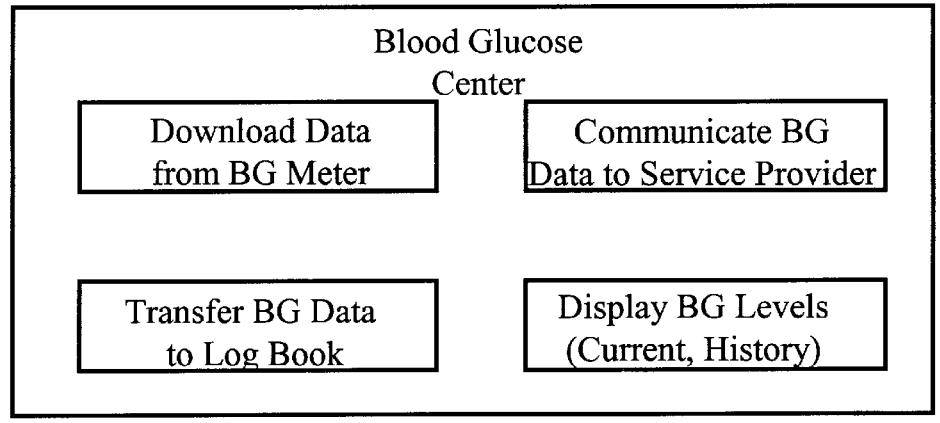
*FIG. 4-D*
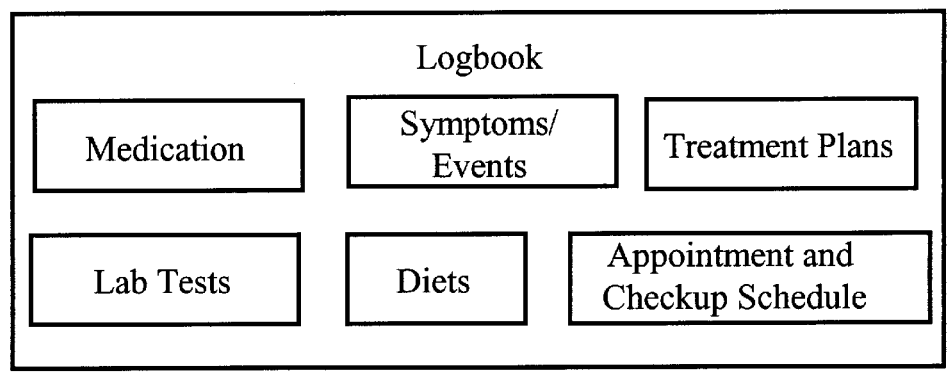
*FIG. 4-E*
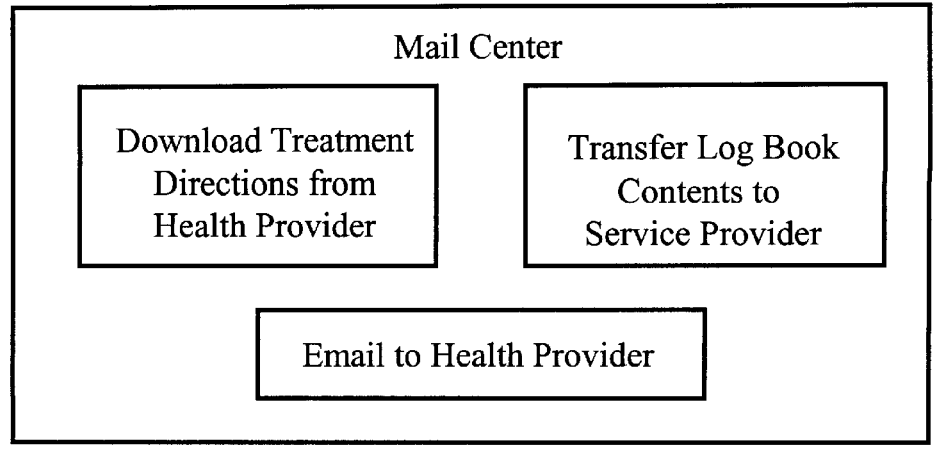

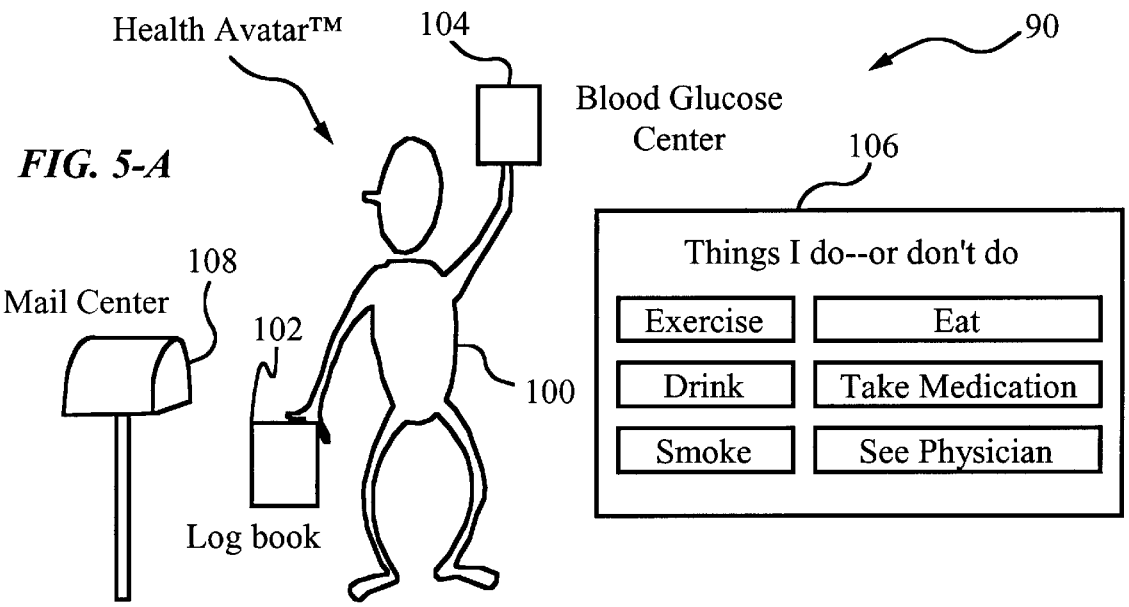
FIG. 5-A
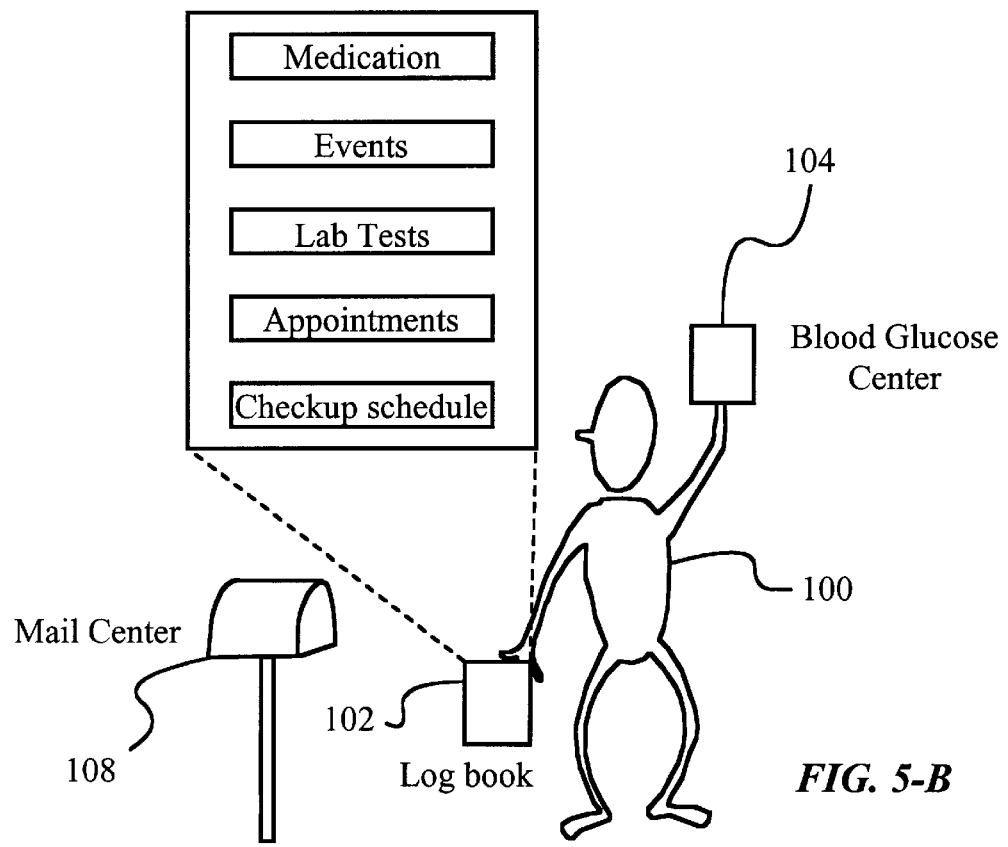
FIG. 5-B

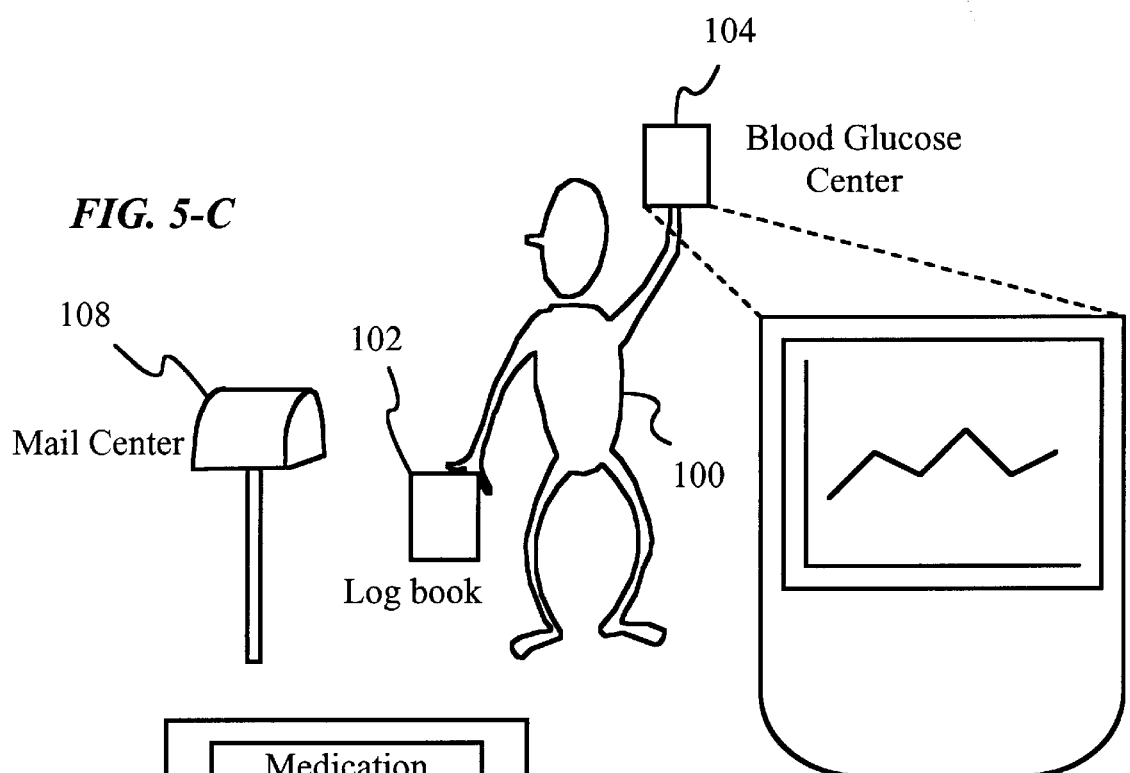
*FIG. 5-C*
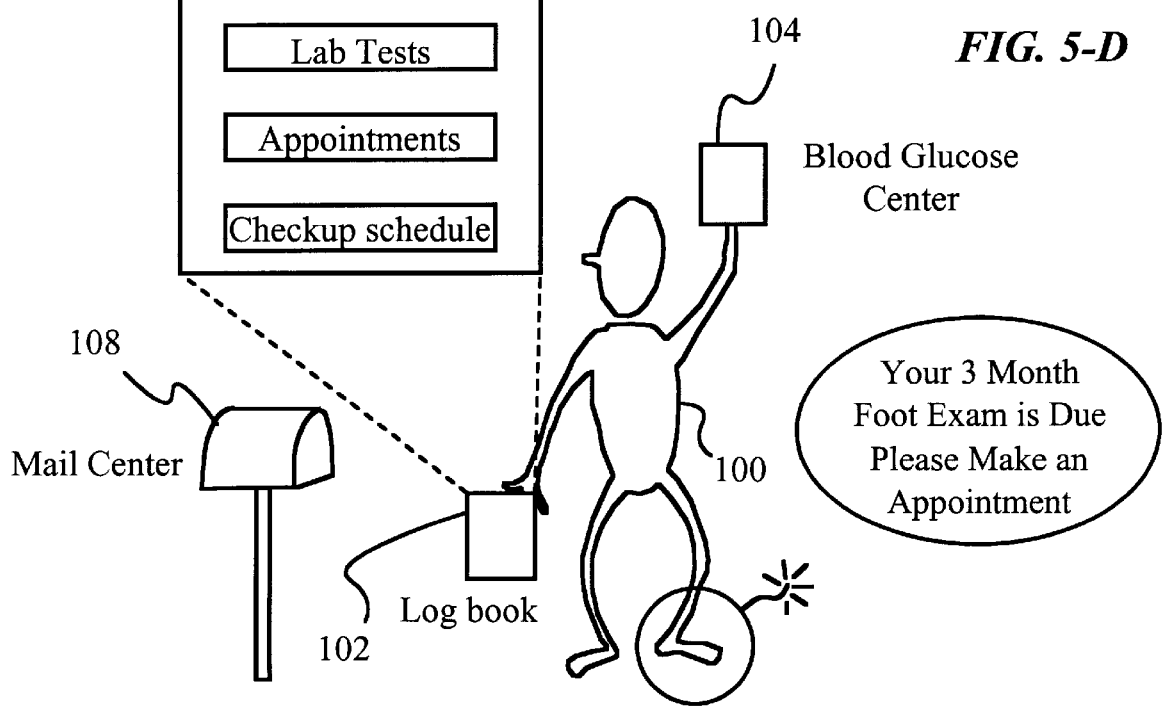
*FIG. 5-D*

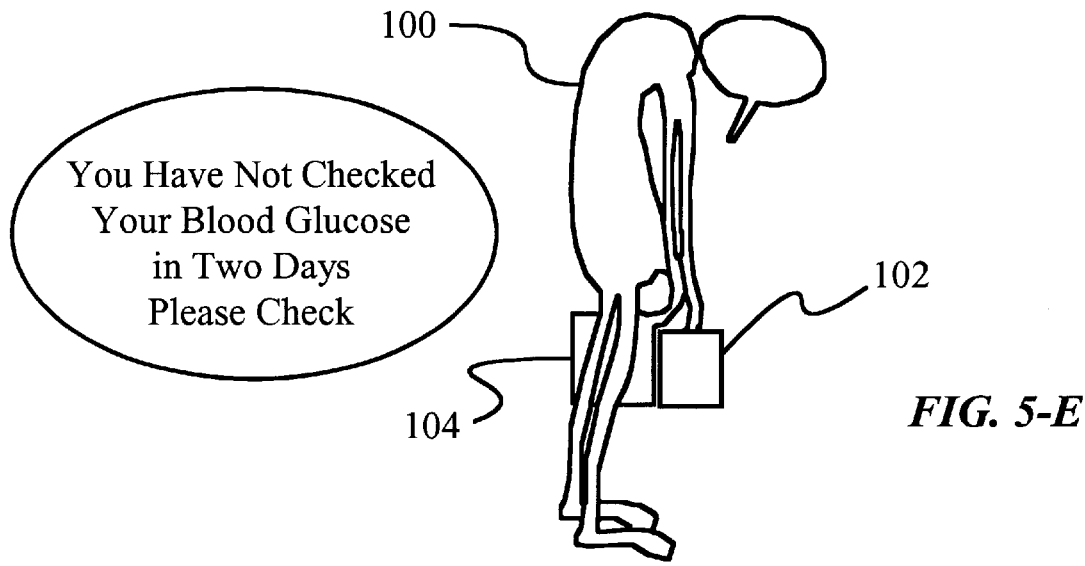
FIG. 5-E
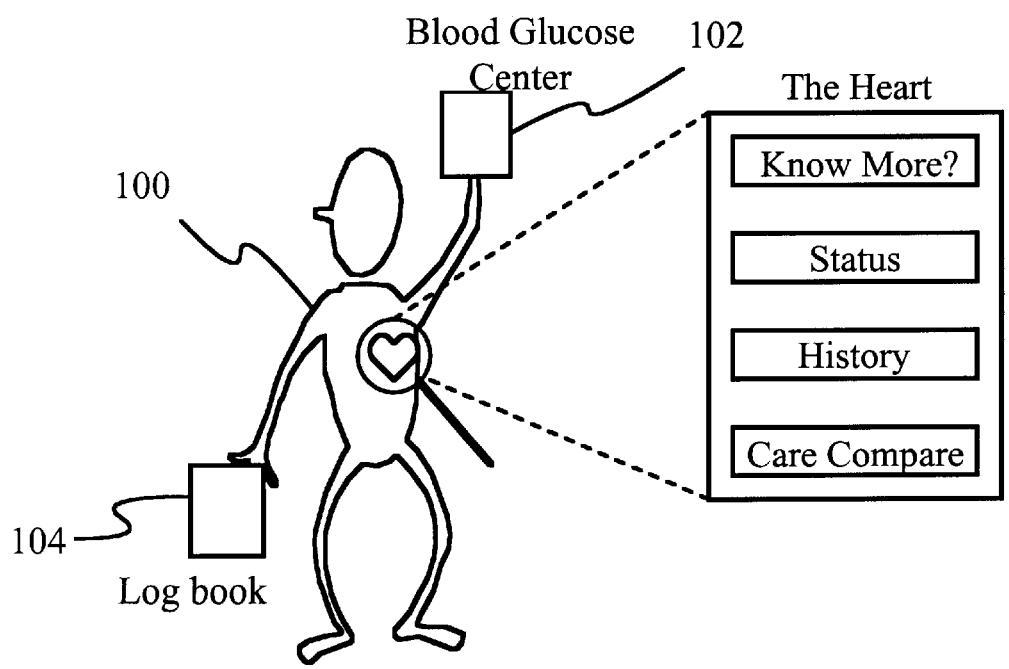
FIG. 5-F

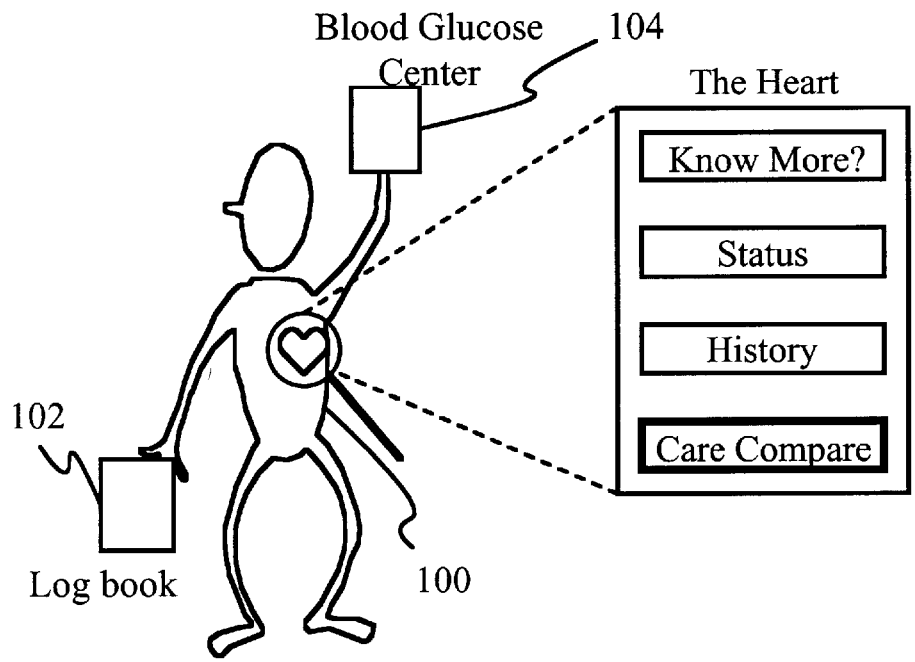

FIG. 5-G

You have searched the database for TESTS done in relation to DIABETES and HEART

1. Heart Exam
43% of people with Diabetes had no heart exam performed in one year.

57% of people with Diabetes had at least one heart exam performed in one year.

More Information?
Press Here for detailed info about the test, including the ADA's recommendations for tests in people with diabetes.

6,032,119

PERSONALIZED DISPLAY OF HEALTH INFORMATION

RELATED APPLICATION DATA

This application is related to co-pending U.S. patent application Ser. No. 08/732,158, entitled "Multiple Patient Monitoring System for Proactive Health Management," by inventor Stephen J. Brown, herein incorporated by reference.

FIELD OF THE INVENTION

This invention relates to computer systems for managing health care, and in particular to a system and method for displaying personalized health information to a patient having a chronic disease or health condition.

BACKGROUND OF THE INVENTION

The health care community has recognized in recent years the importance of preventive care in managing patients' health. Preventive care is particularly important in managing the health of patients having chronic diseases or long-term conditions. Preventive care includes educating patients about their disease, ensuring communication between patients and health care providers (e.g. doctors), and providing patients with tools and/or treatments for managing their disease.

Commonly used preventive care approaches suffer from several drawbacks. Much of health care is voluntary, and thus a large fraction of health care resources is typically spent on patients who are actively seek involvement in their care. A large number of patients do not actively seek information and treatment in the absence of symptoms, however. Also, health providers receive very little information on whether patients are complying with preventive care guidelines. Thus, health providers often are not able to take remedial steps before the disease affects the patients symptomatically (e.g. through pain). Reaching passive patients is thus critical to delivering effective preventive care.

The mass-marketing techniques used for health education by most health maintenance organizations (HMOs) and insurance companies allow little customization of information to an individual patient's needs. Consequently, many patients may not directly identify with the educational approaches used by their health providers. Personalizing health education would significantly raise the effectiveness of preventive care, especially in children and adolescents.

U.S. Pat. No. 5,549,117 to describes a system for communicating health information between health providers and patients having a chronic disease such as asthma. A patient unit displays health information, and communicates health information between the patient and a health provider. The display is relatively impersonal, however.

OBJECTS AND ADVANTAGES OF THE INVENTION

It is a primary object of the present invention to provide a personalized display of a health condition of a patient, such that the patient identifies with the display. It is another object of this invention to provide a method of motivating a patient to follow a prescribed treatment regimen. It is yet another object of this invention to provide a health data display that can be easily comprehended. It is still another object of this invention to provide a system and method for involving patients in their own care, for providing feedback to patients about their health condition, and for monitoring patients' progress in managing their health condition.

SUMMARY OF THE INVENTION

A system of the present invention comprises a set of inputs, a processing means in communication with the inputs, and a display means in communication with the processing means. The set of inputs generate a set of data $\{D[j]\}$, $j=1 \ldots J$. A datum $D[j]$ of the set of data $\{D[j]\}$ characterizes a personal health condition of a patient. The processing means generates a personalized health model of the patient from a generalized health model of the patient and from the data set $\{D[j]\}$. The display means generates a display comprising a body image. The body image illustrates the personalized health model.

The personalized health model is a parameterized model of the health of the individual patient under treatment. The personalized health model is defined by a set of parameters $\{P[k]\}$, $k=1 \ldots K$. The generalized health model is a model of the disease or condition under treatment. The generalized health model is defined by a set of functions $\{f[k]\}$ that specify the dependence of $\{P[k]\}$ on $\{D[j]\}$. That is, $P[k]=f[k](\{D[j]\})$ for all k. The processing means assigns values to the parameters $\{P[k]\}$ using the data $\{D[j]\}$. Parameters suitable for characterizing various diseases include condition of a body part/organ, blood glucose level, respiratory flow, blood pressure, cholesterol level, patient weight, T-cell count, and frequency of health episodes.

The set of inputs comprises a medical record of the patient, as well as records of: a standard of care for the general health condition or disease of the patient, a prescribed treatment of the patient, a display preference, and a personal profile of the patient. The set of inputs further comprises a patient identification means (preferably a card) connected to the display means. The patient identification means specifies the identity of the patient corresponding to a particular display. The patient identification means also specifies a prescribed treatment of the patient and an address of the processing means, allowing a communication between the display means and the processing means. The set of inputs also comprises a patient feedback means (preferably a keyboard) in communication with the processing means, for allowing the patient to communicate a subset of feedback data to the processing means. The feedback means also allows the patient to enter a subset of simulation data characterizing a simulated personal health condition of the patient.

The display means preferably comprises a television set, and a multimedia processor for connecting the television set to the processing means. The display comprises a section assigned to a parameter $P[k]$. In particular, the body image comprises a section assigned to a parameter $P[k]$. A set of characteristics of the body image match a set of predetermined physical characteristics, such that the patient is able to customize the appearance of the body image. Such physical characteristics include age, height, gender, weight, skin color, and hair color. In a particular embodiment, the body image comprises a reproduction of an image of the patient (e.g. a photograph of the patient). In another embodiment, the body image comprises an image of a fictional character.

Preferably, the processing means is in communication with the display means over a remote network, such that the processing means is able to handle processing for multiple display means located at different patient locations. The processing means is in communication with at least some of the set of inputs over a remote network. Processing means at a service provider location can thus access inputs at a health care provider location. A data aggregation means (preferably a database) is in communication with at least some of the inputs and with the processing means. The data aggregation means collects a subset of the data set {D[j]} from the set of inputs, allowing a reduction in the number of direct connections between the processing means and the inputs. The data aggregation means is in communication with the display means over a remote network, so that the data aggregation means stores data for multiple patients.

DESCRIPTION OF THE FIGURES

FIG. 3 shows an alternative architecture of a system of the present invention.

FIG. 4-A depicts the functions of a setup wizard in an embodiment of the present invention.

FIG. 4-B illustrates the functions of a body image module of the present invention.

FIG. 4-C shows the functions of a blood glucose center module of the present invention.

FIG. 4-D shows the functions of a logbook module of the present invention.

FIG. 4-E shows the functions of a mail center module of the present invention.

FIG. 5-A illustrates schematically an introductory screen shot for a diabetes treatment system of the present invention.

FIG. 5-B illustrates the display resulting from the patient's accessing the log book section of the display of FIG. 5-A.

FIG. 5-C illustrates the display resulting from the patient's accessing a subsection of the blood glucose center section of the display of FIG. 5-A.

FIG. 5-D shows a warning resulting from the patient's failure to have a timely foot checkup, according to the system illustrated in FIG. 5-A.

FIG. 5-E shows a warning resulting from a patient's failure to check a blood glucose level according to the patient's treatment plan, according to the system illustrated in FIG. 5-A.

FIG. 5-F shows the display of the system illustrated in FIG. 5-A following the patient's accessing of a display subsection corresponding to the heart.

FIG. 5-G shows the display of the system illustrated in FIG. 5-F following a patient request for comparative care information on the heart.

DETAILED DESCRIPTION

In the ensuing description, the notation (A[j]) is understood to refer to a set of A[j], for j taking some values between a minimum value 1 and a maximum value J. The notation A[j] is understood to refer to some (fixed) j.

Figure 1:
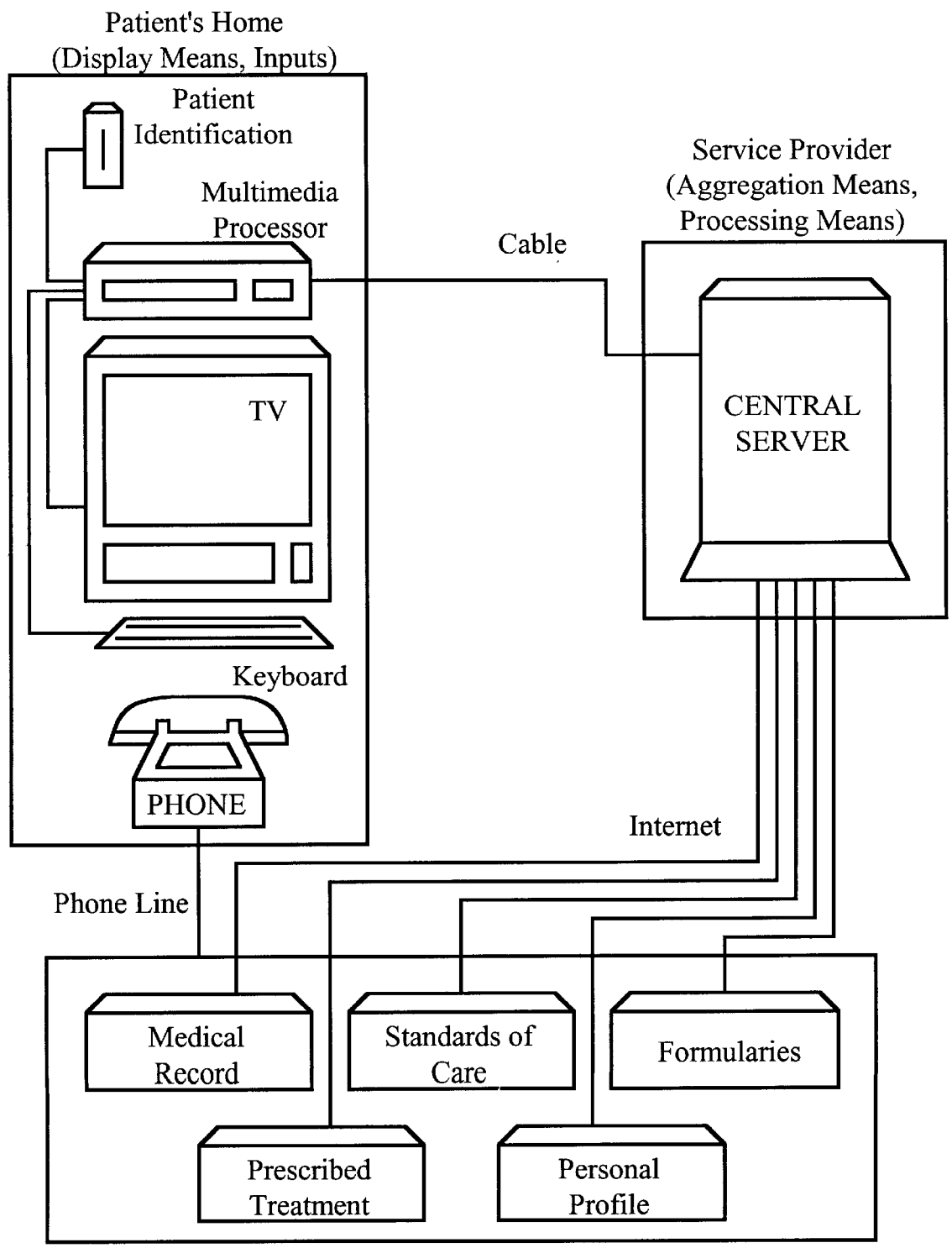
FIG. 1 shows the architecture of a system for health information delivery in a preferred embodiment of the present invention.

FIG. 1 is a schematic diagram illustrating a preferred architecture for a system of the present invention. A processing means (preferably computer software) located on a central server is in communication over remote communication networks with a display means and a set of inputs. The central server processes information for multiple patients, and is thus capable of communicating with multiple display means and input locations. The central server comprises a data aggregation means, preferably a database, in communication with the set of inputs and with the processing means. The data aggregation means collects a subset of the data set {D[j]} from the inputs. Data collected by the data aggregation means is accessed by the processing means. The display means is located at the patient's home. Preferably, the central server is in communication with the health provider over the Internet, and with the patient's home over a cable television delivery line.

The display means preferably comprises a conventional television receiver, and a means for connecting the TV set to a communications network, as illustrated in FIG. 1. Preferably, the TV set is connected to the Internet via a multimedia processor such as a WebTV™ Internet Terminal from WebTV Networks (distributed by Sony). The multimedia processor is in communication over a remote network (such as the Internet, a phone line, or cable used for delivery of cable television programming) with a server at a service provider location.

The multimedia processor connects the processing means on the central server to inputs located at the patient's home: a patient feedback means preferably comprising a keyboard, and a patient identification means preferably comprising a data-bearing card, or "smart card". The multimedia processor has a receiving slot for receiving the patient identification smart card. The patient identification card contains an encrypted patient code, a prescribed treatment for the patient, and a URL address of the processing means. The keyboard allows the patient to provide a subset of feedback data, including display preferences specifying a formatting of the display.

The set of inputs further comprises inputs located at a health care provider location, including records of: a medical history of the patient, a standard of care for a general health condition or disease of the patient, a prescribed treatment for the patient, and a personal profile of the patient. The above-incorporated U.S. patent application Ser. No. 08/732, 158 entitled "Multiple Patient Monitoring System for Proactive Health Management" contains further information on data available to the health care provider.

Examples of data specified by the inputs include blood glucose level histories, generally acceptable blood glucose levels, dates of doctor examinations, generally recommended time periods between doctor examinations, ratings of the patient's interest for a cultural subject (e.g. sports, music), and display customization variables entered by the patient.

Figure 2:
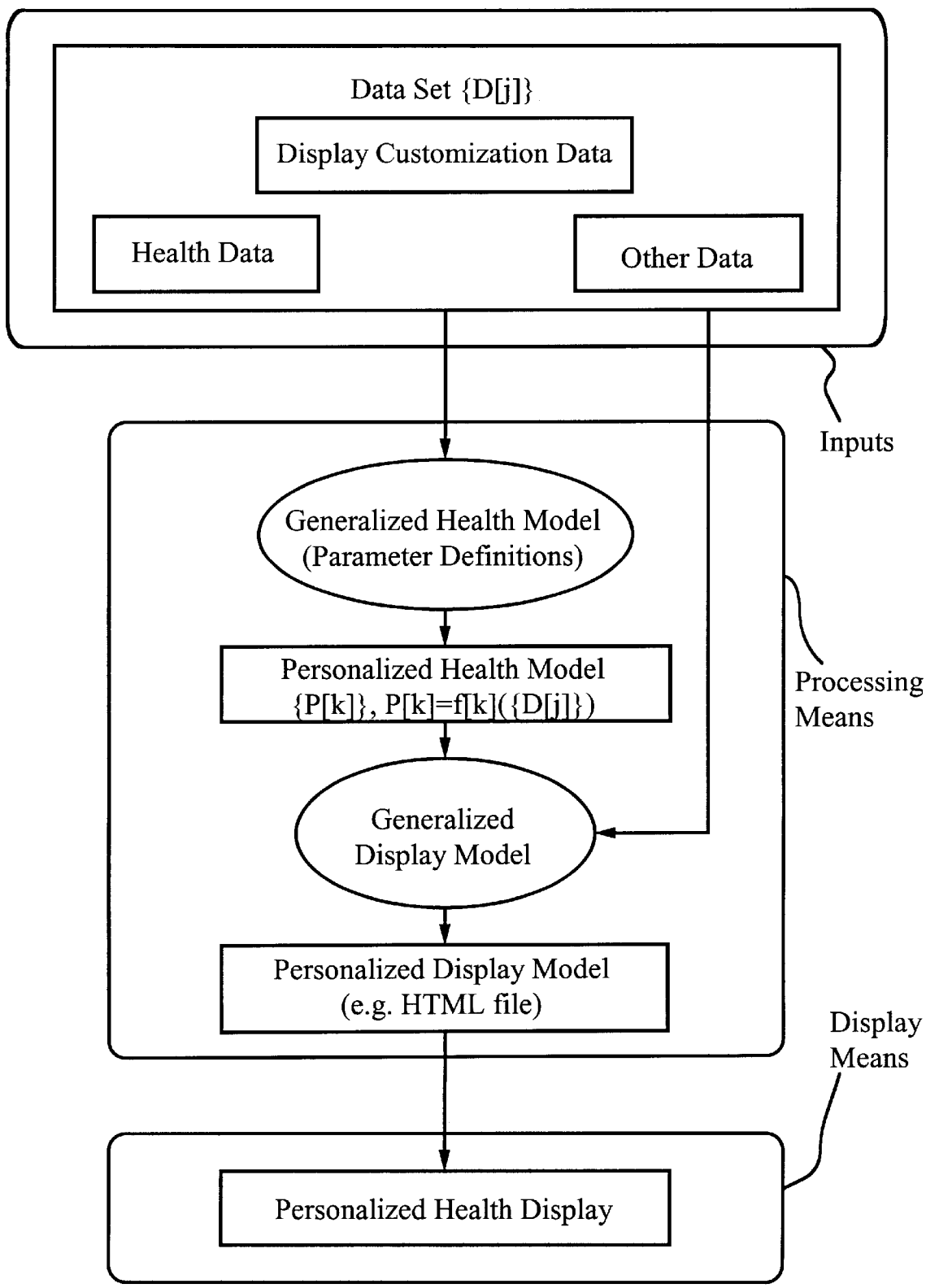
FIG. 2 illustrates processing steps performed on medical and other data to generate a personalized display of the present invention.

FIG. 2 illustrates generally the processing steps performed on the data {D[j]}. A personalized health model of the patient is generated from a generalized health model of the patient's health condition and the patient-specific data {D[j]}. The personalized health model characterizes the patient's current health condition. The personalized health model is defined by a set of parameters {P[k]}, k=1 ... K. In a preferred embodiment designed for diabetes preventive care, suitable parameters include blood glucose level, conditions of body parts or organs (e.g. heart, feet), and compliance with treatment and/or monitoring protocols. Parameters suitable for the characterization of other diseases include respiratory flow in asthma, blood pressure in hypertension, cholesterol in cardiovascular disease, weight in eating disorders, T-cell or viral count in HIV, and frequency or timing of episodes in mental health disorders.

The generalized health model specifies the dependence of the values {P[k]} on the data {D[j]}. The dependence is determined by a set of functions {f[k]}, where P[k]=f[k]({D

[j]}) for all k. That is, the value P[k] of the kth parameter is specified in general by a function f[k]. The function f[k] has as its argument the set of data {D[j]}, i.e. f[k] depends on at least one datum D[j] The forms of the functions {f[k]} can be readily determined by the skilled artisan according to the disease under treatment.

For example, parameter P[1] may measure the latest recorded blood glucose level of the patient, and the datum D[1] may be the latest blood glucose level recorded in the patient's medical record. Then the function f[1]({D[j]})=D[1], and P[1]=D[1]. Parameter P[2] may measure the health condition of the patient's feet, which may be defined to depend on parameters such as blood glucose level (D[1]), the time between doctor checkups (D[2]), and some other parameter D[j]. Then P[2]=f[2]{D[j]}=f[2](D[1], D[2], D[j]), wherein the exact form of the function f[2] is specified by the generalized health model.

Using the set of parameters {P[k]} and a generalized display model of the patient, the processing means generates a personalized display model of the patient. The personalized display model preferably comprises an HTML file encoding a display comprising a body image. Generating displays using HTML is well known in the art, and will not be discussed here in detail. The formatting of the body image is preferably customized to the targeted patient, such that the patient identifies with the body image. A set of the characteristics of the body image matches a set of predetermined characteristics. In particular, body image characteristics preferably match physical characteristics chosen by the patient. Such characteristics include age, height, gender, weight and/or build, skin color, hair color, and identity (if any) of a fictional character. In one embodiment, the body image is a schematic figure representing the patient. In other embodiments, the body image is a reproduction (e.g. a photograph) of the patient's appearance, a representation of a cartoon or fictional character, or a representation of a character in a field of interest of the patient (e.g. a favorite basketball player or movie actor).

The body image illustrates the personalized health model of the patient. In particular., the body image comprises sections assigned to body parts/organs of the patient. The image sections graphically represent the health conditions of the corresponding patient parts. Particular characteristics (e.g. color, shape, blinking rate) of the image sections are determined by the set of values {P[k]}. In general, each section of the body is assigned to at least one parameter P[k]. The body image is preferably an image map, such that the patient can access information on a body part or organ by clicking on the corresponding section of the body image.

In an embodiment suitable for the treatment of a diabetes patient, an unacceptable value of a parameter measuring a health condition of the patient's feet leads to a display of swollen feet on the body. The body's feet blink if the time period since the last doctor checkup is longer than a predetermined threshold. In an embodiment suitable for dental hygiene education, the teeth in the body image are represented to be black if a value P[k] measuring a health condition of the patients' teeth is below a predetermined threshold. The appearance of the entire body is used to characterize the personal health condition of the patient. For example, for a patient having low blood glucose levels the corresponding body is displayed to be tired.

In an embodiment used for simulating the effects of hypothetical health decisions or events on the patient's health condition, the data set {D[j]} includes a subset of simulation data characterizing a simulated personal health condition of the patient. The displayed body then contains information on the simulated health condition of the patient. The simulation can be used by the patient to examine, among others, the effects of hypothetical changes in behavior (e.g. diet and sleep patterns) on the patient's health condition.

FIG. 3 shows schematically an alternative system for delivering personalized health information, according to the present invention. A personal computer at the patient's home comprises aggregation, processing and display means. The keyboard of the personal computer is an input. Other inputs are at a remote location, and are in communication with the computer over a remote network. An HTML page illustrating the patient's personalized health model is generated on the patient's computer by the processing means.

A particular user interface of a system of the present invention is illustrated in FIGS. 4 and 5. FIGS. 4-A through 4-E illustrate the functions provided by Health Avatar™, a diabetes management application. FIGS. 5-A through 5-G are schematic depictions of screen shots from the same application, illustrating the functions of the application.

As shown in FIG. 4-A, a setup wizard is used by the patient to customize the appearance of the body image, and to enter configuration information for hardware and software in communication with the application. Hardware includes a blood glucose meter, a modem, a printer, while software includes a communications applications for communicating with health care providers and service providers.

The body image itself (the Health Avatar™) displays actual or simulated health information of the patient, according to actual or simulated health data (see FIG. 4-B). The patient can use a blood glucose center (FIG. 4-C) to download information from a blood glucose meter, to transfer blood glucose data to the service provider database, to transfer blood glucose data to a logbook, and to display current blood glucose levels or a history of blood glucose levels. A log book (FIG. 4-D) allows the patient to access and modify records of medication, symptoms/events, lab tests, treatment plans, diets, and appointment and checkup schedules. A mail center (FIG. 4-E) is used by the patient to download treatment directions from the health provider, to transfer log book contents to the service provider and/or the health provider, and to communicate by-e-mail with the health provider.

FIG. 5-A is a schematic depiction of a screen shot 90 of the Health Avatar™ application. The display comprises several sections: a body image section 100, a log book section 102, a blood glucose center section 104, a feedback section 106, and a mail center section 108. The patient accesses functions of the application by clicking on corresponding display sections or subsections.

The functions of the log book module become accessible if the patient clicks on log book section 102, as illustrated in FIG. 5-B. A similar display (not shown) is generated if the patient clicks on blood glucose center section 104. FIG. 5-C illustrates the display after the patient accesses the "Display Blood Glucose Level" (see FIG. 4-C) subfunction of the blood glucose center. Feedback section 106 (FIG. 5A) enables the patient to record information about his or her health habits.

Body image 100 comprises subsections corresponding to the patient's organs and/or body parts. If a particular body part of the patient requires attention or care, the corresponding subsection of body image 100 is highlighted. FIG. 5-D depicts the application display if the diabetes patient neglects care of his or her feet. A display subsection corresponding to the patient's feet blinks, and the patient is prompted to make an appointment with a care provider.

The overall appearance of body image section 100 depends on the blood glucose level of the patient, and on the time since the last recording of the patient's blood glucose level. FIG. 5-E illustrates the application display if the patient fails to record or download his or her blood glucose levels according to a treatment plan.

FIG. 5-F schematically depicts the application display if the patient clicks on a subsection of body image 100 corresponding to the patient's heart. The patient can request general information about the heart in diabetes patients, about the current and historical conditions of his or her heart, and about other patients approaches to the hearts' care.

FIG. 5F schematically depicts a display following a patient's request, from the display depicted in FIG. 5E, for general information about other patient's approaches to care of the heart.

It will be clear to one skilled in the art that the above embodiment may be altered in many ways without departing from the scope of the invention. For example, many relative placements of the aggregation, processing, and display means may be suitable in a system of the present invention. In particular, the data aggregation means may be in communication with the processing means over a remote network. Suitable parameters, data sets, and processing functions can be readily determined by the skilled artisan for various applications. Systems and methods of the present invention are suitable for the management of any chronic disease or condition requiring regular medical attention and patient compliance with a treatment plan, including diabetes, asthma, AIDS, heart and cardiovascular disease, weight control programs, mental health conditions, attention deficit disorder, smoking, and substance abuse. Many display and patient input implementations, including non-HTML-based implementations, can be suitable for use with the present invention. Accordingly, the scope of the invention should be determined by the following claims and their legal equivalents.

What is claimed is:

1. A system for displaying health information, comprising:
   a) a set of inputs for generating a set of data $\{D[j]\}, j=1 \ldots J$, wherein a datum $D[j]$ of said set of data $\{D[j]\}$ characterizes a personal health condition of a patient and, wherein said set of inputs comprises a patient feedback means and a patients feedback generates a subset of said set of data;
   b) a processing means in communication with said set of inputs, said processing means for generating a personalized health model of said patient from a generalized health model of said patient and from said set of data $\{D[j]\}$; and
   c) a display means in communication with said processing means, for generating a display comprising a body image, said body image illustrating said personalized health model, said body image comprising an image map including at least one body part or organ, wherein said patient can access information on said at least one body part or organ by interacting with a section of said body image on said display means.

2. The system of claim 1, wherein said personalized health model comprises a set of parameters $\{P[k]\}, k=1 \ldots K$, and wherein said generalized health model specifies a dependence of said set of parameters $\{P[k]\}$ on said set of data $\{D[j]\}$.

3. The system of claim 2, wherein said processing means is adapted to assign values to said set of parameters $\{P[k]\}$ using said set of data $\{D[j]\}$.

4. The system of claim 2, wherein said set of parameters $\{P[k]\}$ comprises a blood glucose level of said patient.

5. The system of claim 2, wherein said set of parameters $\{P[k]\}$ comprises a condition of a body part of said patient.

6. The system of claim 2, wherein said set of parameters $\{P[k]\}$ comprises a parameter selected from the group consisting of respiratory flow, blood pressure, blood glucose level, cholesterol level, patient weight, T-cell count, and frequency of health episodes.

7. The system of claim 1, wherein said set of inputs comprises a patient identification means for specifying an identity of said patient, and wherein said patient identification means is in communication with said display means.

8. The system of claim 7, wherein said patient identification means is adapted to specify a prescribed treatment of said patient.

9. The system of claim 7, wherein said patient identification means comprises a card.

10. The system of claim 7, wherein said patient identification means is in communication with said display means, and said patient identification means is adapted to specify an address of said processing means for allowing communication between said display means and said processing means.

11. The system of claim 1, wherein said display means comprises a television set, and a multimedia processor for connecting said television set to said processing means.

12. The system of claim 1, wherein said set of data $\{D[j]\}$ comprises a subset of simulation data characterizing a simulated personal health condition of said patient.

13. The system of claim 1, wherein said display and said body image each comprise a section assigned to a parameter $P[k]$.

14. The system of claim 1, wherein a set of characteristics of said body image match a set of predetermined physical characteristics of said patient.

15. The system of claim 14, wherein said set of physical characteristics comprises a characteristic selected from an age, a height, a gender, a weight, a skin color, and a hair color.

16. The system of claim 1, wherein said body image comprises a reproduction of a photograph of said patient.

17. The system of claim 1, wherein said body image comprises an image of a sports personality or an image of a movie actor.

18. The system of claim 1, wherein said processing means is in communication with said display means and with said set of inputs over at least one remote network.

19. The system of claim 1, further comprising a data aggregation means in communication with said set of inputs and with said processing means, said data aggregation means for collecting a subset of said set of data $\{D[j]\}$ from said set of inputs, wherein said data aggregation means is in communication with said display means over a remote network.

20. The system of claim 1, further comprising at least one additional display means, wherein said at least one additional display means is in communication with said processing means over a remote network.

21. The system of claim 1, wherein said processing means is located at a location remote from said display means.

22. The system of claim 1, further comprising a central server located at a location remote from said display means, wherein said central server includes said processing means and an aggregation means, and said central server is in communication with said display means over a remote network.

23. The system of claim 22, wherein said display means is located at a home of said patient.

24. The system of claim 23, wherein said display means comprises a conventional television receiver.

25. The system of claim 21, wherein said display means further comprises a multimedia processor including an Internet terminal, said multimedia processor is connected to said conventional television receiver, and said central server is in communication with a health provider over the Internet.

26. The system of claim 22, wherein said central server is in communication with said display means over a cable television delivery line.

27. The system of claim 1, wherein said patient is a diabetes patient, and wherein the condition of said at least one body part or organ is impacted by diabetes.

28. The system of claim 27, wherein said at least one body part or organ is the heart or a foot.

29. The system of claim 1, wherein said set of inputs comprises a record selected from the group consisting of a medical record of said patient, a record of a standard of care for a general health condition of said patient, a record of a prescribed treatment of said patient, a record of a display preference, and a record of a personal profile of said patient.

30. The system of claim 1, wherein said body image is a personalized body image representing the patient, said display means displaying said personalized body image for viewing of said personalized body image by the patient, wherein the patient identifies with said personalized body image.

31. The system of claim 1, wherein said display further comprises a health care parameter section, a logbook section, a feedback section, and a mail center section.

32. The system of claim 31, wherein said logbook section is adapted for use by said patient to access and modify records of: medication, symptoms/events, lab tests, treatment plans, diet, and appointment and checkup schedules; wherein said mail center section is adapted for use by the patient to download treatment directions from a health provider, to transfer logbook contents to the service provider and/or to the health provider, and to communicate by e-mail with the health provider; and wherein said feedback section is adapted for use by the patient to record information about his or her health habits.

33. The system of claim 31, wherein said health care parameter section comprises a blood glucose center section, said blood glucose center section adapted for use by said patient to: download information from a blood glucose meter, transfer blood glucose data to a service provider database, transfer blood glucose data to a logbook, display current blood glucose level, and to display a history of blood glucose levels.

34. A method of providing personalized health information to a patient, said method comprising the steps of:
   a) generating a set of data $\{D[j]\}$, $j=1 \ldots J$, from a set of inputs, wherein a datum $D[j]$ of the set of data $\{D[j]\}$ characterizes a personal health condition of a patient;
   b) generating a personalized health model of the patient, wherein the personalized health model is generated by a processing means from a generalized health model of the patient and from the set of data $\{D[j]\}$;
   c) generating a display on a display means, wherein the display is generated by the processing means, and wherein the display comprises a body image, the body image illustrating the personalized health model of the patient; and
   d) having the patient view the body image on the display means, wherein the patient relates personally to the personalized health model illustrated by the body image and, wherein said the body image comprises an image map such that the patient can access information on at least one body part or organ of the body image by interacting with a section of the body image on the display means.

35. The method of claim 34, wherein the processing means comprises software located at a central server remote from the display means.

36. The method of claim 34, wherein the display means comprises a television set coupled to a multimedia processor.

37. The method of claim 34, wherein the set of inputs are entered via a keyboard of a personal computer or via a smart card.

38. The method of claim 34, wherein the display further comprises a health care parameter section, a logbook section, a feedback section, and a mail center section.

39. The method of claim 38, further comprising the step of:
   c) accessing data, by the patient, from the health care parameter section, the logbook section, or the mail center section.

40. The method of claim 38, further comprising the step of:
   d) inputting data, by the patient, via the health care parameter section, the logbook section, the feedback section, or the mail center section.

41. A system for displaying a personalized health model of a patient to the patient, comprising:
   a) a set of inputs for generating a set of data $\{D[j]\}$, $j=1 \ldots J$, wherein a datum $D[j]$ of said set of data $\{D[j]\}$ characterizes a personal health condition of a patient, wherein said set of inputs comprises a first set of inputs and a second set of inputs, said first set of inputs located at a home of the patient, and said first set of inputs comprising a patient identification means and a patient feedback means, and wherein said second set of inputs are located at a health care provider remote from a home of the patient, and said second set of inputs selected from the group consisting of a medical record of said patient, a record of a standard of care for a general health condition of said patient, a record of a prescribed treatment of said patient, a record of a display preference, and a record of a personal profile of said patient;
   b) a central server including a processing means in communication with said set of inputs, said processing means for generating a personalized health model of a patient from a generalized health model of the patient and from said set of data $\{D[j]\}$; and
   c) a plurality of display means, each of said plurality of display means located at a location remote from said processing means and in communication with said processing means over a remote network, each of said plurality of display means for generating a display comprising a body image illustrating said personalized health model of a patient, wherein said body image comprises an image map.

42. The system of claim 41, wherein said processing means generates a personalized display model comprising a personalized body image of the patient for displaying on said display means, wherein said personalized body image includes a set of characteristics which match physical characteristics chosen by the patient, said personalized body image is personalized for viewing by the patient and the patient identifies personally with said personalized body image.

* * * * *